United States Patent [19]

Berg

[11] Patent Number: 5,425,855

[45] Date of Patent: Jun. 20, 1995

[54] SEPARATION OF ETHYL BENZENE FROM P-XYLENE BY EXTRACTIVE DISTILLATION

[75] Inventor: Lloyd Berg, 1314 S. Third Ave., Bozeman, Mont. 59715

[73] Assignee: Lloyd Berg, Bozeman, Mont.

[21] Appl. No.: 224,708

[22] Filed: Apr. 8, 1994

[51] Int. Cl.[6] ............................ B01D 3/40; C07C 7/08
[52] U.S. Cl. ...................................... 203/62; 585/805; 585/808; 585/864
[58] Field of Search .................. 203/62; 585/864, 805, 585/808

[56] References Cited

U.S. PATENT DOCUMENTS

| | | | |
|---|---|---|---|
| 2,763,604 | 9/1956 | Dorsey et al. | 203/60 |
| 4,292,142 | 9/1981 | Berg | 203/51 |
| 4,299,668 | 11/1981 | Berg | 203/51 |
| 4,959,128 | 9/1990 | Berg | 203/60 |
| 4,966,656 | 10/1990 | Berg | 203/60 |
| 5,397,441 | 3/1995 | Berg | 203/57 |

*Primary Examiner*—Wilbur Bascomb, Jr.

[57] ABSTRACT

Ethyl benzene is difficult to separate from p-xylene by conventional distillation or rectification because of the closeness of their boiling points. Ethyl benzene can be readily separated from p-xylene by extractive distillation. An effective agent is 5-methyl-2-hexanone, also called methyl isoamyl ketone.

1 Claim, No Drawings

SEPARATION OF ETHYL BENZENE FROM P-XYLENE BY EXTRACTIVE DISTILLATION

FIELD OF THE INVENTION

This invention relates to a method for separating ethyl benzene from p-xylene using 5-methyl-2-hexanone as the agent in extractive distillation.

DESCRIPTION OF PRIOR ART

Extractive distillation is the method of separating close boiling compounds from each other by carrying out the distillation in a multiplate rectification column in the presence of an added liquid or liquid mixture, said liquid(s) having a boiling point higher than the compounds being separated. The extractive agent is introduced near the top of the column and flows downward until it reaches the stillpot or reboiler. Its presence on each plate of the rectification column alters the relative volatility of the close boiling compounds in a direction to make the separation on each plate greater and thus require either fewer plates to effect the same separation or make possible a greater degree of separation with the same number of plates. The extractive agent should boil higher than any of the close boiling liquids being separated and not form minimum azeotropes with them. Usually the extractive agent is introduced a few plates from the top of the column to insure that none of the extractive agent is carried over with the lowest boiling component. This usually requires that the extractive agent boil about twenty Celcius degrees or more higher than the lowest boiling component.

At the bottom of a continuous column, the less volatile components of the close boiling mixtures and the extractive agent are continuously removed from the column. The usual methods of separation of these two components are the use of another rectification column, cooling and phase separation, or solvent extraction.

Extractive distillation typically requires the addition of an equal amount to twice as much extractive agent as the ethyl benzene & p-xylene on each plate of the rectification column. The extractive agent should be heated to about the same temperature as the plate into which it is introduced. Thus extractive distillation imposes an additional heat requirement on the column as well as somewhat larger plates. However this is less than the increase occasioned by the additional agents required in azeotropic distillation.

Ethyl benzene boils at 136° C.; p-xylene boils at 138° C. The closeness of their boiling points give them a relative volatility of 1.08. Table 1 shows the relative volatility required to get 99% purity. By straight rectification, 160 actual plates are required for the ethyl benzene—p-xylene separation but with an extractive agent that increases the relative volatility to 1.3 for example, only 47 actual plates are required.

TABLE 1

Theoretical and Actual Plates Required vs. Relative Volatility for Ethyl Benzene - p-Xylene Separation

| Relative Volatility | Theoretical Plates Required At Total Reflux, 99% Purity | Actual Plates Required, 75% efficiency |
|---|---|---|
| 1.08 | 120 | 160 |
| 1.3 | 35 | 47 |

OBJECTIVE OF THE INVENTION

The object of this invention is to provide a process or method of extractive distillation that will enhance the relative volatility of ethyl benzene from p-xylene in their separation in a rectification column. It is a further object of this invention to identify organic compounds which in addition to the above constraints, are stable, can be separated from p-xylene and recyled to the extractive column and reused with little decomposition.

SUMMARY OF THE INVENTION

The objects of this invention are provided by a process for separating ethyl benzene from p-xylene which entails the use of 5-methyl-2-hexanone, also called methyl isoamyl ketone, as the agent in extractive distillation.

DETAILED DESCRIPTION OF THE INVENTION

I have discovered that 5-methyl-2-hexanone, also called methyl isoamyl ketone, will greatly improve the relative volatility of ethyl benzene to p-xylene and permit the enhanced separation of ethyl benzene from p-xylene by rectification when employed as the agent in extractive distillation.

WORKING EXAMPLES

Example 1

Sixty-five grams of ethyl benzene, 15 grams of p-xylene and 40 grams of 5-methyl-2-hexanone were chaged to a vapor-liquid equilibrium still and refluxed for thirteen hours. Analysis indicated a vapor composition of 60.5% ethyl benzene, 39.5% p-xylene, a liquid composition of 53.1% ethyl benzene, 46.9% p-xylene. This is a relative volatility of ethyl benzene to p-xylene of 1.35.

Example 2

A solution comprising 40 grams of ethyl benzene, 80 grams of p-xylene was placed in the stillpot of a 5.6 theoretical plate glass perforated plate rectification column. 5-Methyl-2-hexanone as the extractive agent was pumped in continuously. The overhead temperature was 103° C. and the stillpot temperature was 145° C. After 1.5 hours of steady operation, overhead and stillpot samples were taken and analysed. The overhead composition was 17.7% ethyl benzene, 82.3% p-xylene and the stillpot composition was 4.9% ethyl benzene, 95.1% p-xylene. This gives a relative volatility of ethyl benzene to p-xylene of 1.29.

I claim:

1. A method for recovering ethyl benzene from a mixture of ethyl benzene and p-xylene which comprises distilling a mixture of ethyl benzene and p-xylene in the presence of about one part by weight of an extractive agent per part of ethyl benzene—p-xylene mixture, recovering the ethyl benzene as overhead product and obtaining the p-xylene and the extractive agent from the stillpot, wherein said extractive agent is 5-methyl-2-hexanone.

* * * * *